April 15, 1975 E. H. PALACKY Plant Pat. 3,705
PEAR TREE
Filed March 21, 1974
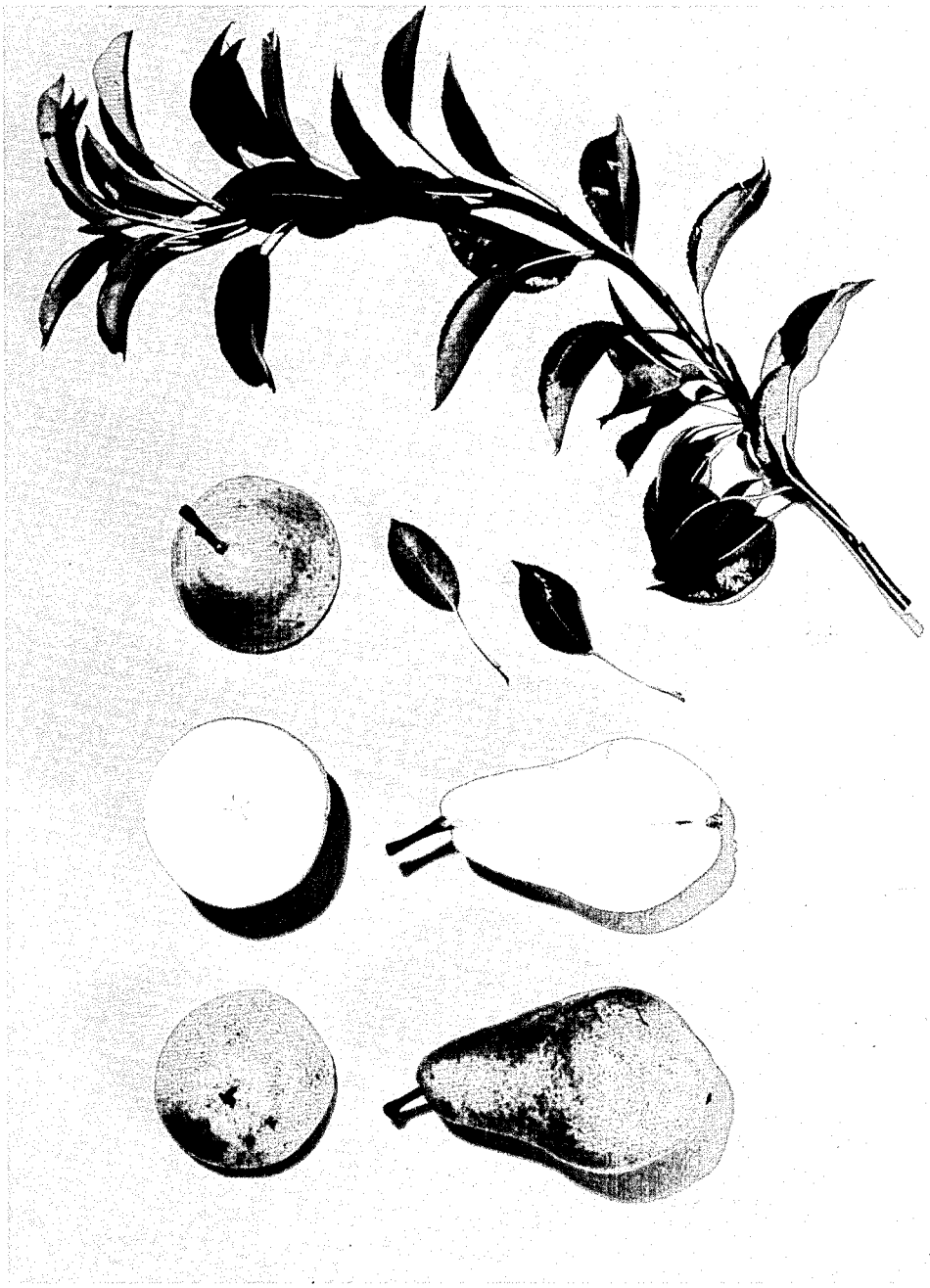

United States Patent

Plant Pat. 3,705
Patented Apr. 15, 1975

3,705
PEAR TREE

Edward H. Palacky, Farmington, Mich., assignor to Hilltop Orchards & Nurseries, Inc.

Filed Mar. 21, 1974, Ser. No. 453,559
Int. Cl. A01h *5/03*
U.S. Cl. Plt.—36 1 Claim

The present invention relates to a new and distinct variety of pear tree discovered as a whole tree in a block of regular "Bartlett" variety pear trees, said discovery having been made in the orchard of Edward Palacky, Farmington, Mich., in 1964.

The original tree, about twenty-five years old, apparently developed from a shoot of a "Bartlett" rootstock. It appears that two or three years after the orchard was planted, this particular tree was damaged, causing a strong shoot to develop from below the graft union. Presumably, the original trees were budded on "Bartlett" seedlings so that this "Spartlet" tree is probably not a mutation, but rather a seedling. Since the fruit of this seedling had some "Bartlett" characteristics it was referred to as "Bartlett-x" for the first seven years of testing of second generation trees. In 1971 it was suggested that it be called "Spartlet," which has a connotation of "Bartlett," and also includes the first syllable of Spartan, the Michigan State University's athletic teams. Trees propagated from the original "Spartlet" tree have been observed and tested in second generation orchards by Michigan State University and Gerber Products Company.

The drawing herein (color photograph) shows a typical example of fruit and foliage of the new variety.

The following is a detailed description of "Spartlet."

TREE

Shape: The "Spartlet" shoot growth is reddish brown with a few large conspicous lenticels and short pointed buds. Mature branches (3 years and older) turn silvery gray with intermittent brown streaks. Pointed one-inch spurs are formed on second year growth, and these thicken and develop into fruit spurs on three and four year old wood. Often, shoots one to eight inches long, with a fruit purse at the end, develop on four year and older branches. Main scaffold branches are spreading with current shoot growth often curving laterally. These growth characteristics produce a spreading tree of medium size and one which requires minimum training and pruning. "Spartlet" trees, to date have been shown to be comparatively free of fire blight, but not resistant. The parent tree, having been heavily cut for scion wood, has produced vigorous growth relatively blight free as compared to other trees in the same orchard.

Leaf: The leaves resemble those of "Bartlett" having fine serrate, nearly smooth margins and shiny leathery appearance and are about twice as long as they are wide.

Flower: The flowers are large, showy white with large red anthers slightly subtending the style. Full bloom usually occurs two days later than "Bartlett." As all flowers do not open uniformly there seems to be enough overlap for cross-pollination with "Bartlett."

FRUIT

Shape: The fruit is large, reaching 3.3 inches in diameter and 4.2 inches long with a one inch stem. Fruit blocky, pyriform with a long, narrow neck.

Skin: The skin is smooth, dark greenish yellow (Nickerson 10Y 7/9) with a strong greenish yellow (Nickerson 7.5Y 7/9) blush. Numerous pin-pointed russet lenticels.

Flesh: The flesh is slightly aromatic, fine-grained to granular in non-ripened stage, changing to smooth, buttery and slightly fibrous when fully ripened.

Core: The core is medium to large and fleshy with small seed cavities.

Seed: The seed is small, slender, dark brown.

Calyx: The calyx is closed and shallow.

Quality: Fruit quality equal to "Bartlett," ripening mid-September about twelve days after "Bartlett."

Storage: Fruit, which matures mid-September in Michigan, has stored well until mid-February at 31° F. in regular storage. For eating out-of-hand, the "Spartlet" fruit must be well ripened under humidity and temperature condition.

Use: The storage quality, large size, and bright blush appearance of the fruit suggest that "Spartlet" may have fresh market value and perhaps use in special gift packages in December. "Spartlet" fruit has been processed into puree and sliced canned halves under pilot test in commercial processing plants in Michigan and found to make acceptable packs of these products.

In summary: The "Spartlet" pear has a new and unique combination of desirable characteristics including fruit which matures mid-September and stores well until mid-February, large size and fruit quality equal to "Bartlett."

"Spartlet" trees have been shown to be comparatively free of fire blight, but not resistant. Evidence shows that "Spartlet" is self fruitful but requires wind or insect pollen transfer. It is productive, the original tree having borne six to nine bushels annually, and top worked trees starting to fruit in the third and fourth years.

I claim:

1. A new and distinct variety of pear tree substantially as shown and described.

No references cited.

ROBERT E. BAGWILL, Primary Examiner